United States Patent [19]

Lang et al.

[11] Patent Number: 4,822,598

[45] Date of Patent: * Apr. 18, 1989

[54] COSMETIC AGENT ON THE BASIS OF QUATERNARY CHITOSAN DERIVATIVES, NOVEL QUATERNARY CHITOSAN DERIVATIVES AS WELL AS PROCESSES FOR MAKING SAME

[75] Inventors: Günther Lang, Reinheim; Harald Wendel, Ober-Ramstadt; Eugen Konrad, Darmstadt, all of Fed. Rep. of Germany

[73] Assignee: Wella Aktiengesellschaft, Darmstadt, Fed. Rep. of Germany

[*] Notice: The portion of the term of this patent subsequent to Nov. 14, 2005 has been disclaimed.

[21] Appl. No.: 634,100

[22] PCT Filed: Nov. 3, 1983

[86] PCT No.: PCT/EP83/00287

§ 371 Date: Jul. 20, 1984

§ 102(e) Date: Jul. 20, 1984

[87] PCT Pub. No.: WO84/02343

PCT Pub. Date: Jun. 21, 1984

[30] Foreign Application Priority Data

Dec. 10, 1982 [DE] Fed. Rep. of Germany ....... 3245784

[51] Int. Cl.$^4$ .......................... A61K 7/06; A61K 7/09; A61K 7/13; C08B 37/08
[52] U.S. Cl. .......................................... 424/47; 8/405; 8/406; 424/70; 424/71; 424/72; 514/844; 514/847; 514/937; 514/944; 536/20

[58] Field of Search ...................... 424/70, 47; 536/20; 514/958

[56] References Cited

PUBLICATIONS

Anikeera, Chem. Abs., 1975, vol. 82, pp. 45565x.

*Primary Examiner*—Dale R. Ore
*Attorney, Agent, or Firm*—Michael J. Striker

[57] ABSTRACT

The invention relates to cosmetic agents for treating of hairs or the skin which is characterized by a content of novel quaternary chitosan derivatives of the formula $$HO[C_6H_{11-m}NO_4(R^1)_m(R^2)_n(R^3)_q]_p H$$

($m=0-0.5$; $n=0-6$; $q=0.005-3.0$; $p=10-50,000$; $R^1=$acetyl; $R^2=-CH_2CH(OH)-CH_2-O-$, $-CH_2-CH(CH_2OH)-O-$ or $-CH(CH_2OH)-CH_2-O-$; $R^3=$

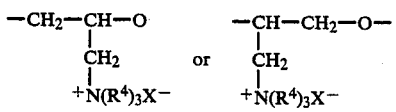

with $R^4=C_1$- to $C_4$-alkyl and $X=Cl$, $Br$, or $CH_3SO_4$.

It relates in furtherance to the novel quaternary chitosan derivatives as well as processes for making the same. These chitosan derivatives have a good substantivity, among others, to hair keratin and show hair strengthening and hair conditioning characteristics.

15 Claims, No Drawings

COSMETIC AGENT ON THE BASIS OF QUATERNARY CHITOSAN DERIVATIVES, NOVEL QUATERNARY CHITOSAN DERIVATIVES AS WELL AS PROCESSES FOR MAKING SAME

The invention relates to cosmetic agents for treating hairs or the skin with a content of novel macromolecular quaternary compounds derived from chitosan in a suitable cosmetic base.

In furtherance, the invention relates to the novel quaternary chitosan derivatives as well as processes for making same.

It is already known to use in cosmetic agents cation active polymers, in particular polymers which have the quaternary ammonium groups as a conditioning agent, in particular for the treatment of hairs. Due to an interaction between their ammonium groups and the anionic groups of the hair, the cation active polymers have a great affinity to the keratin fiber.

It had been found that the use of such cation active polymers in such cosmetic agents results in numerous advantages; the disentanglement of the hairs as well as the treatment thereof is facilitated and in furtherance the hair gets elasticity and a shiny effect. Due to the affinity to keratin these polymers tend to collect in the hairs after repeated application, so that they become heavier which is undesirable in the end effect.

In furtherance, problems exist with synthetic polymers because of the physiological effect of eventually existing monomer traces which are hardly removable from the polymer.

It was already tried to eliminate these aforementioned disadvantages in that water soluble salts of the chitosan are used in such cosmetic agents, i.e. a polyglucosamin by deacetylation of chitin. In this context, reference is made to applicants' European Pat. No. 0 002 506 as well as their German Pat. No. 26 27 419.

In the same manner as in the majority of the cation active polymers with quaternary grouping, chitosan also very often has the disadvantage that it is less compatible with the anionic active surface active agents which customarily are used in cosmetic agents for treating hairs, in particular in shampoos. It is therefore required to use the effect of chitosan in separate treatments, namely before and/or after the shampooing.

Furthermore, chitosan prooves to be practically unsoluble in neutral and alkalic medium, so that its application, for example, in alkalic permanent wave agents or hair dying agents is not possible. It is an object of the invention to eliminate these disadvantages.

While conducting continuous tests with chitosan and the compounds derived therefrom it was found that certain quaternary chitosan derivatives do not have the aforementioned disadvantages.

Therefore, with these quaternary chitosan derivatives cosmetic agents can be made for treating of hair or the skin which are characterized by surprisingly advantageous characteristics and which are characterized in that in a suitable cosmetic base a quaternary macromolecular polymer compound derived from chitosan is contained having the general formula I $$HO[C_6H_{11-m}NO_4(R^1)_m(R^2)_n(R^3)_q]_pH, \qquad (I)$$

wherein m denotes any given numerical value from 0 to 0.5, n denotes any given numerical value from 0 to 6, q is a given numerical value from 0.005 to 3.0, p denotes a whole number from 10 to 50,000, $R^1$ is an acetyl residue, $R^2$ represents a bivalent residue $-CH_2CH(OH)-CH_2-O-$,

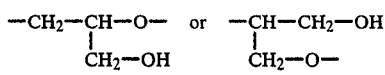

and $R^3$ is a bivalent residue

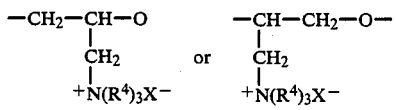

with $R^4 = C_1$- to $C_4$-alkyl and $X = Cl$, Br, I or $CH_3SO_4$.

The agents which contain the quaternary chitosan derivatives of formula 1 in accordance with the invention are generally suitable for treating the skin and/or hairs. For example, they may be present as hair- and/or body washing agent, tinting shampoos, hair dressing creams, hair dressing lotions, hair drier lotions, agents for setting the hair, wash lotions, hair treatments, agents against dandruf, agents for permanent hair styling, agents for dyeing or decoloring of hairs, agents for applying before or after the hair dyeing and as cosmetic agents for care, for protection or for cleansing the skin like skin tonic lotions, shaving lotions, moisture creames, coldcreames, body lotions, sun protection agents or also make-up preparations like make-up creams and rouges.

The content of the novel chitosan derivatives of formula I in the cosmetic agents in accordance with the invention is advantageously 0.05 to 10% by weight, preferably 0.05 to 3.0% by weight.

The cosmetic agents in accordance with the subject invention may contain, in addition to the novel chitosan derivatives of formula I for making a cosmetic base, all those constituents which are customarily used, in particular anionic, cationic, amphoteric, amphoteric ions or nonionic surface active tensides, foam synergists, stabilizers, sequestration agents, pigments, thickeners, emulsifiers, buffer substances, conservation agents, dyes, perfume oils, known cosmetic polymers, like anionic, nonionic, kationic or amphoteric polymers, natural substances, cosmetic oils, fatty alcohols, paraffins, foam stabilizers, active substances against dandruff, reducing agents and propellent gases.

The cosmetic agents in accordance with the invention preferably have a pH-value of 2 to 11 and may be available in form of aqueous, alcoholic or watery-alcoholic preparations, for example, with an alcohol with 1 to 4 carbon atoms, as solutions, as creames, as gels, as dispersions or as emulsions. It is also possible to spray these agents with the aid of a sprayer or other suitable spray devices or as a mixture with customary propellent gases as an aerosol spray from a pressurized containers.

When the cosmetic agents in accordance with the invention are agents for setting hair, like liquid hair setting lotion or hair spray, they are customarily available as aqueous or watery-alcoholic solutions, which are characterized by a content of quaternary chitosan derivatives of the aforementioned formula I. Thereby, the quaternary chitosan derivatives themselves may be used as a film forming or setting resin. However, additional other film forming natural or synthetic polymers may be used in the hair setting agent in accordance with the invention. As natural polymers shellac, alginates, gelatines, pektines and cellulose derivatives are taken into consideration, for example. Of the synthetic polymers polyvinylpyrrolidone, polyvinylacetate, polyacrylic compounds, like acrylic acid- or methacrylic acid polymerisates, basic polymerisates of ester from acrylic acid or methacrylic acid with amino alcohols or the salts or quaternisation products of these basic polymerisates, polyacrylnitrile as well as co- or terpolymerisates from such compounds, for example, polyvinylpyrrolidonevinylacetate are used, for example. The agents then have a pH value between 6 and 8. Such agents for setting the hair customarily contain film forming polymers in a total amount of about 0.05 to 3.0% by weight. If the agents contain other film forming polymers in addition to the quaternary chitosan derivatives of the formula I, the content of quaternary chitosan derivatives is reduced accordingly.

The alcohols used, are particularly the customarily used lower alcohols which are used for cosmetic purposes, like ethyl alcohol and isopropyl alcohol.

The agents for setting the hair in accordance with the invention may also have the customary additives like, for example, perfume oils, bactericides or fungicides, combability improving substances etc.

The agents for setting the hair in accordance with the invention may also simultaneously dye or tint the hair by a content of cosmetic dyes. Such preparations are commercially known, among others, as dyeing or tinting strengtheners. They additionally contain known dyes customary for hair setting like, for example, aromatic nitro dyes (for example, 1,4-diamino-2-nitrobenzene), azo dyes (for example, C.I. Acid Brown 4), anthraquinone dyes (for example, C.I. Disperse Violet 4) and triphenylmethan dyes (for example, C.I. Basic Violet 1), whereby the dyes of these classes may have an acid, nonionogenic or basic character, depending on the type of their substitutes. Their total concentration in these preparations is customarily about 0.01 to 2.0% by weight.

The agents for setting the hair in accordance with the invention have an improved substantivity toward the hair, a particularly good combability and a good feel of the hair in the wet stage as well as a particularly pleasant feel of the hair in the dried stage, have an equally good setting of the hair with respect to customary agents.

When the agents in accordance with the invention are hair washing agents they will be available in form of watery solutions or emulsions and contain, in addition to the novel chitosan derivativesmat least an anionic, kationic, nonionic, or amphoteric tenside.

In this hair washing agent the concentration of the tenside is generally between 3 and 50% by weight and preferably between 3 and 25% by weight, with respect to the total weight of the agent, whereby the pH-value is generally between 3 and 9 and preferably between 4 and 7.

The agents which are present in the form of hair washing agents in accordance with the invention generally contain different additional substances, in particular perfumes, conservation substances, thickeners, foam stabilizers, buffer substances, cosmetic resins, pigments and dyes.

Among the foam stabilizers, the fatty amides and in particular the mono- or diethanol amides of copra fatty acids, lauryl- or oleic acid mono- or diethanol amide may be mentioned which are advantageously used in amounts of 1 to 10 and preferably 1 to 3% by weight, with respect to the total weight of the agent.

Among the thickeners, in particular the acryl polymers and the cellulose derivatives, like carboxymethyl cellulose, hydroxy propyl methyl cellulose, hydroxyethyl cellulose may be mentioned. The thickeners are generally present in a constituent of 0.1 to 5% by weight.

Among the tensides or surface active agents, which may be used in combination with the novel quaternary chitosan derivatives, the following may be mentioned by way of example:

(a) the anionic surface active agents like, for example, the alkali- or earth alkali salts of the alkanolamine of alkanesulfonates, alkylsulfates and alkylether sulfates, the $C_{12}$–$C_{18}$-alkyl- and, in particular $C_{12}$–$C_{14}$-alkylsulfate sodium salts of triethanol amine salts, the sodium or triethanol amine salts of lauryl- or tetradecylether sulfates, the dinatrium salt of the sulfosuccinic semi-esters of alkanol amides, the soaps and the polyether carboxylic acid;

(b) the nonionic surface active agents like, for example, oxyethylated fatty alcohols with 12 to 18 carbon atoms, for example, with up to 40 Mol ethyenoxide per Mol fatty alcohol, oxyethylated laurin-, tetradecyl-, cetyl-, olein-, palmitin and stearin alcohol, alone or in a mixture, the fatty alcohols of oxyethylated lanolin or oxyethylated lanolin; polyglycerylether of saturated or unsaturated fatty alcohols and alkyl phenols with 8 to 30 carbon atoms in the alkyl residue and 1 to 10 glycerin units in the molecule, as well as fatty acid alkanol amide;

(c) the cationic surface active agents like, for example the dilauryl dimethyl ammonium chloride, the chlorides or bromides of alkyl dimethyl benzyl ammonium, the chlorides or bromides of alkyl trimethyl ammonium, for example, cetyl trimethyl ammonium chloride or bromide, tetradecyl trimethyl ammonium chloride or bromide, the alkyl dimethyl hydroxy ether ammonium chloride or bromide, the dialkyl dimethyl ammonium chloride or bromide, alkylpyridinum salts, for example, cetyl pyridinum chloride, the alkyl amide ethyl trimethyl ammonium ether sulfate, imidazolin derivatives, compounds with a cationic character, like aminoxide, for example, alkyl dimethyl aminoxide or alkyl aminoethyl dimethyl aminoxide, (d) the amphoteric or zwitterionic surface active agents like, for example the carboxyl derivatives of imidazol, the N-alkylbetaines, the N-alkylsulfobetaines, the N-alkylaminobetaines, the N-alkylaminopropionates, the alkyl dimethyl ammonium acetate or the $C_{12}$–$C_{18}$-alkyl dimethyl carboxy methyl ammonium salts.

The cosmetic agents in accordance with the invention may also represent creames or lotions as use for hair treatment or skin treatment agent. They are then mostly available in form of oil-in water- or water-in-oil emulsions or suspensions and contain, in addition to the novel chitosan derivatives of formula I, cationic, nonionogenic, amphoteric or anionic emulsifiers, as well as a constituent of the oil phase, for example, fatty alcohols, fatty acid ester- or amide, furthermore perfume oils, petrolatum, wool fatty alcohol or solid or liquid paraffines.

When the agents in accordance with the invention represent hair dyeing agents or hair tinting agents, they are preferably available in form of creames or lotions and contain additional customary hair dye substances from the group of the aromatic nitro dyes, azo dyes, anthra quinon dyes, triphenyl methan dyes or also oxidation dyes, for example, from the group of the aromatic diamide or aminophenole. Furthermore, these agents may contain, if need be, alkalisation agents, antioxidants, as well as further cosmetic additives and auxiliary substances which are customary for such agents.

The agents in accordance with the invention may also represent permanent shaping agents or fixing agents for hairs. They then contain, in addition to the mentioned chitosan derivatives of formula I, reducing agents, like thioglycolic acid, thiolactic acid, ammonium sulfite or oxidation agents, like hydrogen peroxide or sodium bromide as well as, if need be, alkalisation agents or peroxide stabilizers, for example, phosphoric acid and other cosmetic auxiliary substances and additional substances like, for example, perfume oils, odoriferous substances, treatment substances and dyes.

As already mentioned, the cosmetic agents in accordance with the invention may also be used for treatment of the skin.

Indeed, these cosmetic agents facilitate the moistening of the skin and avoid drying out. These agents also give the skin an excellent softness in feel.

The cosmetic agents in accordance with the invention are available in form of creams, gels, emulsions or watery, alcoholic, or watery-alcoholic solutions which contain the chitosan derivative of formula I in a concentration of 0.1 to 10% by weight and preferably of 0.2 to 6% by weight.

The auxiliary substances which are generally contained in these cosmetic preparations are, for example, odorous substances dyes, preservatives, thickeners, sequestration agents, emulsifiers, sun protection filters etc.

These preparations are made by applying classical techniques.

By way of example, for forming a cream one could use a watery phase which contains the chitosan derivative in accordance with the invention and, if need be, contains other constituents or auxiliary substances in a dissolved form, and to emulsify an oily phase.

Different compounds may be used for the oily phase, for example, paraffin oil, vaselin oil, oil of sweet almonds, avacado oil, olive oil, fatty acid ester, like glycerylmonostearate, ethyl palmitate or isopropyl palmitate or alkylmyristate, like propylmyristate, butylmyristate or cetylmyristate. One can also compound them with fatty acid alcohols, like cetyl alcohol or paraffins, for example, bees wax.

The chitosan derivatives of formula I may be contained in the cosmetic preparations for the skin treatment either as an auxiliary substance or as the main active ingredient.

The novel chitosan derivatives contained in the cosmetic agent in accordance with the invention are derived from chitosan which is obtained by deacetylization of chitin a naturally occuring acetyl glucosamine.

The chitosan is nonsoluble in the neutral and alkalic medium, however because on account of its chemical nature it forms in the acid medium salts with organic and inorganic acids which, for example, are used in the paper and textile industry as additives, as well as also as coagulants for suspensions, as chelat former for heavy metal ions, as well as in medicine and in cosmetics (see in this context the publication of Muzarelli: "Chitin", Pergamon Press, 1977).

Some water soluble chitosan derivatives are known, for example carboxy methyl chitosan, sulfoethyl chitosan (see Nud ga, Plisko and Darnilov, Zhur. Prikl. Khim. 47, 872–875). These water soluble chitosan derivatives are changed in their ionic character or are physiologically questionable (Epichlohydrinchitosan, publication of Noguchi, Arato and Komai; Kogyo Kagaku Zasshi 72, 769–799 and Japanese patent application No. 43-39 322, H. Haga).

These aforementioned polymer compounds require relative expensive processes for their technical manufacturing.

It was now found that by reaction of chitosan with a glycidyl trialkyl ammonium halogenide (oxyranmethanammonium-N,N,N-trialkyl halogenide) of the formula

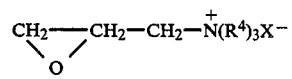

($R^4 = C_1$ to $C_4$-alkyl; $X = Cl$, Br, I or $CH_3SO_4$) as well as, if need be, additionally with glycidol (1,2-epoxypropanol-3) one can make, in a simple manner, quaternary chitosan derivatives with a high substantivity, among others, to hair keratin.

The novel quaternary macromolecular polymer compounds which are derived from chitosan are characterized by the general formula I $$HO[C_6H_{11-m}NO_4(R^1)_m(R^2)_n(R^3)_q]_pH, \qquad I$$

wherein m denotes any given numerical value from 0 to 0.5, n denotes any given numerical value from 0 to 6, q is a given numerical value from 0.005 to 3.0, p denotes a whole number from 10 to 50,000, $R^1$ is an acetyl residue, $R^2$ represents a bivalent residue —CH$_2$CH(OH)—CH$_2$—O—,

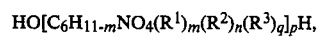

and $R^3$ is a bivalent residue

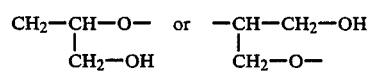

with $R^4 = C_1$- to $C_4$-alkyl and $X = Cl$, Br, I or $CH_3SO_4$, whereby the expression in brackets represents repeating substituted glucosamine-monomer units, The novel quaternary chitosan derivatives containing nitrogen are made in accordance with the invention in that a chitosan consisting of 50-100% deacetylated chitin is reacted in the presence of a solvent with a glycidyl trialkyl ammonium halogenide, as well as, if need be, in addition with glycidol in a suitable ratio. If the reaction is performed in the presence of glycidol, a solvent is not required, whereby a surplus of glycidol may be used as solvent.

Suitable glycidyl trialkyl ammonium halogenides are, for example, glycidyl trimethyl ammonium chloride and glycidyl triethyl ammonium chloride. The epoxide which contain the quaternary nitrogen may be made in situ by reacting the corresponding chlor compound with basic catalysts (for example, reaction of 1-chlor-3-trimethyl ammonium-propanol-2-chloride with a sodium hydroxide solution) before or during the reaction with the chitosan.

The reaction of the chitosan with glycidol and the quaternary epoxyde can be performed in a simple manner by a simultaneous reaction with both components, but it is also possible to perform the reaction in 2 stages. The chitosan may be at first reacted with the glycidol and the obtained product with the quaternary epoxide or a mixture of glycidol and the quaternary epoxide, or the base chitosan may be reacted only with the quaternary epoxide and, if need be, subsequently with glycidol.

For this purpose, the chitosan is advantageously used in finely powdered form. The reaction itself can be performed at temperatures between 10° and 100° C., preferably between 50° and 80° and this temperature is maintained advantageously under stirring for 2 to 100 hrs. The reaction may be performed with or without acid or basic catalysts in the presence of solvents or, if using a surplus of glycidol, also without a special solvent.

However, the reaction is preferably performed in the presence of water. However, it had been shown to be advantageous to operate without any additional catalysts, whereby the ratio of chitosan to water is between 1:0.05 and 1:100 and the ratio of chitosan with respect to the total amount from the glycidol and the glycidyl trialkyl ammonium halogenide (with respect to the Mols of substitutable amino groups on the chitosan) between 1:0.5 and 1:30, preferably between 1:1 and 1:10. If the chitosan should be reacted with glycidol, the ratio between the glycidol and the glycidyl trialkyl ammonium halogenide should, depending on the desired degree of substitution, advantageously be between 1:10 and 10:1.

Although the performance of the reaction is preferred in the presence of water, it can be performed by using other solvents wherein at least one of the reaction products is soluble. Examples for such solvents are alcohols, like ethanol, methanol, glycol and glycerin as well as ketones, for example, methylethyl ketone and acetone.

In accordance with another embodiment of the process in accordance with the invention for making chitosan derivatives of the formula I, additional organic or inorganic acids or bases are added as catalysts.

Suitable acids to be used as catalysts are, for example, hydrochloric acid, lactic acid and formic acid. Examples of suitable bases are trialkyl amines like, for example, trimethyl amine, triethyl amine or tryalkylolamines as well as alkalihydroxide and earthalkali hydroxide. It is basically also possible to start with water soluble salts of the chitosan, for example, chitosan lactate, chitosan acetate, chitosan hydrochloride etc. Thereby, a larger amount of the glycerin ester of the used acid may be generated as a side product, so that the cleaning of the generated reaction products is made more difficult.

The preparation of the reaction mixture may be performed, for example, in a manner whereby the solvent and, if need be, surplus glycidol is distilled off the reaction mixture in a vacuum.

When making water soluble quaternary chitosan derivatives the reaction product can be dissolved in a preferred manner in a surplus of water and can be separated from the unsoluble reaction residue by filtration or centrifugation. As further steps for cleaning the reaction products the watery solutions may be dialized and/or isolated by precipitation in acetone, alcohols or other organic solvents, after reducing the watery solution.

In accordance with a particularly advantageous embodiment of the manufacturing process in accordance with the invention a structural modified chitosan is used as a base material made by reprecipitation and deep freezing. The reaction runs in a particularly advantageous manner and with a particularly good yield with such a base material.

The process for making the novel quaternary chitosan derivatives in accordance with the invention will be explained in more detail in conjunction with the following examples.

EXAMPLE 1

Quaternization of chitosan with glycidyl trimethyl ammonium chloride 100 g (0.62 mol) chitosan with a limit viscosity number $\eta = 140$ ml/g (determined in DIN-Ubbelohde viscosimeter with 0.2 m acetic acid and 0.1 m sodium acetate as a solvent) and a free amine content of 86% were reacted in a double casing stirring vessel in 1 liter water with 228 g glycidyl trimethyl ammonium chloride. The adding of glycidyl trimethyl ammonium chloride was carried out in 3 portions of 76 g each at an interval of 2.5 hours. The reaction mixture was stirred at a temperature of 60° C. for 24 hours. Thereafter the starting material was adjusted to a pH value of 5.4 with hydrochloric acid and filtered through gauze. The reaction product was precipitated into aceton by instilling the watery solution, vacuumed off and finally dried in a vacuum at 50° C. 115 g of the quaternary chitosan derivative were obtained.

| Characteristic data of the quaternary chitosan derivative | |
|---|---|
| Limit viscosity number: | $\eta = 27$ ml/g |
| Titratable nitrogen: | 3.15 nmol/g |
| Chloride determination: | 13.17% (= 3.7 mmol/g) |
| Degree of substituion calculated therefrom: | 1.4 |

The steam absorption of a film was 22.45% at 80% air moisture with respect to 30% air moisture. The pendulum hardness in accordance with König was at 17 sec.

For calculating the degree of substitution one first determines the Mol amount on tritratable nitrogen $N_t$ [nmol/g] by nonwatery titration with perchloric acid. The mean molecular weight of a substituted chitosan unit is calculated therefrom as follows:

$$\overline{M} \frac{g}{[mol]} = \frac{1000}{N_t \frac{[nmol]}{g}}$$

Furthermore the equation

| | |
|---|---|
| $\overline{M} = 161 + x \cdot 152 + y \cdot 74 + z \cdot 42$ | |
| molecular weight of a chitosan unit = | 161 [g/mol] |
| molecular weight of a quaternary group $R^3$ from formula I ($R^4 = CH_3$, X = Cl) = | 152 [g/mol] |
| molecular weight of a glycidol group $R^2$ from formula I | 74 [g/mol] |

-continued

| | |
|---|---|
| molecular weight of a CO—CH$_2$—group = | 42 [g/mol] | x = degree of substitution, cationic groups R$^3$
y = degree of substituion, glycidol groups R$^2$
z = degree of substitution of the chitosan used with acethyl groups (at 60–96% free amino groups, the degree of substitution is 0.04–0.4)

For calculating the degree of substitution with cationic groups R$^3$ one uses the chloride titration with the ion sensitive chloride electrode. The following applies:

$$x = \frac{[Cl^-] \times M}{1000}$$

From this, the degree of substitution with glycidol groups can be calcuIates as follows:

$$y = \frac{\bar{M} - 161 - 152 \cdot x - 42 \cdot z}{74}$$

EXAMPLE 2

Reaction of chitosan with glycidol and glycidyl trimethyl ammonium chloride 100 g (0.62 mol) chitosan ($\eta$=140 ml/g; free amine 86%) were reacted with 79.5 g (1.07 mol) glycidol and 80.6 g (0.53 mol) glycidyl trimethyl ammonium chloride in 1 liter water at 30° C. by stirring for 48 hours. Subsequently further 26.3 g (0.36 mol) glycidol and 25.8 g (0.17 mol) glycidyl trimethyl ammonium chloride were added and further stirred for another 24 hours at 40° C. The alkalic reacting reaction mixture was adjusted to a pH value of 5.5 with hydrochloric acid. The obtained solution was dialysed for 1 week (dialyse hose, separating limit 1000) and the quaternary chitosan derivative is recovered by precipitation in aceton, suctioning off and drying (at 50° C. in the vacuum). The yield of the clear water soluble quaternary chitosan derivative was 115 g.

| Characteristic data of the quaternary chitosan derivative | |
|---|---|
| Limit viscosity number: | $\eta$ = 65 ml/g |
| titratable nitrogen: | 3.07 mmol/g |
| chloride determination: | 2.35% (= 0.69 mmol/g |
| degree of substitution: | |
| cationic groups | 0.22 |
| glycidol group | 1.7 |
| steam absorption: | 11.1% |
| pendulum hardness according to Konig | 201 sec. |

EXAMPLE 3

50 g (0.31 mol) chitosan with the same characteristic data as in example 2 were stirred in a double casing vessel with 31.5 ml (0.47 mol) glycidol and 141.4 g (0.93 mol) glycid trimethyl ammonium chloride as well as 500 ml water for 24 hours at a temperature of 80° C. Subsequently, the reaction mixture was centrifuged and the residue, consisting of nonreacted chitosan, was removed. The watery solution was dialized for 1 week and subsequently prepared, as described in example 2. The yield of the quaternary chitosan derivative was 35.7 g.

| Characteristic data of the quaternary chitosan derivative | |
|---|---|
| Limit viscosity number | $\eta$ = 41 ml/g |
| Titratable nitrogen: | 2.18 mmol/g |
| Chloride determination: | 8.88 (= 2.48 mmol/g) |
| Degree of substitution: | |
| cationic groups | 1.10 |
| glycidol groups | 1.6 |

EXAMPLE 4

A quaternary chitosan from example 1 is additionally reacted with glycidol 20 g quaternary chitosan from example 1 are dissolved in 100 ml water and was brought to reaction at 50° C. under stirring with 50 ml (0.76 mol) glycidol for 48 hours. Subsequently, the reaction mixture was dialyzed for 1 week and further prepared as described in example 2. The yield of the quaternized chitosan derivative was 8.8 g.

| Characteristic data of the quaternary chitosan derivative | |
|---|---|
| Limit viscosity number: | $\eta$ = 51 ml/g |
| Titratable nitrogen: | 3.01 mmol/g |
| Chloride determination: | 6.4% (= 1.8 mmol/g) |
| Degree of substitution: | |
| cationic groups | 0.6 |
| glycidol groups | 1.0 |

EXAMPLE 5

First of all, a glycercyl-chitosan with the characteristic data $\eta$=55 ml/g, degree of substitution 1.7 is made in the following manner:

100 g chitosan ($\eta$=140 ml/g; free amine 86%) were reacted in a double casing stirring vessel with 450 ml glycidol (Mol ratio 1:9) and the mixture was stirred for 96 hours at a temperature of 80° C. The reaction product was introduced into about 5 l water and the insoluble residue was centrifuged off. The watery solution was reduced and the reaction product was isolated by precipitation in aceton. After drying in a vacuum at 50° a yield of 60 g was obtained.

50 g of thid glycercyl-chitosan was dissolved in 200 ml water. 5 g Ba(OH)$_2$.8H$_2$O and 23 g glycidyl trimethyl ammonium chloride were added and the mixture was stirred for 24 hours at 50° C. The obtained watery solution was instilled in aceton. The precipitated quaternary chitosan derivative was suctioned off and dried at 50° C. in a vacuum. The yield was 37 g.

| Characteristic data of the quaternary chitosan derivative | |
|---|---|
| Limit viscosity number: | $\eta$ = 35 ml/g |
| Titratable nitrogen: | 2.45 mmol/g |
| Chloride determination: | 1.5 mmol/g |
| Degree of substitution: | |
| cationic groups | 0.6 |
| glycidol groups | 2.0 |
| Water steam absorption: | 19.6% |
| Pendulum hardness according to Konig | 158 sec |

EXAMPLE 6

High molecular chitosan is dissolved with hydrochloric acid and again precipitated with a sodium-hydroxide solution. Thereafter, it is reacted with glycidol and glycidyl trimethyl ammonium chloride.

15 g of a high molecular chitosan with the chracteristic data $\eta=600$ ml/g and 76% of free amine were dissolved in 1 liter water with the equimolar amount of hydrochloric acid and subsequently precipitated with a sodium hydroxide solution by adjusting a pH value of 10. The precipitated and suctioned off water containing chitosan was stirred for 15 hours at 80° C. with 22 ml glycidol as well as 24.2 g glycidyl trimethyl ammoniumchloride. Thereafter, the chitosan was completely dissolved. This watery solution was instilled into aceton. The precipitated cationic chitosan derivative was suctioned off and dried in a vacuum at 50° C. The yield of the novel chitosan derivative was 22 g.

| Characteristics of the quaternary chitosan derivative | |
|---|---|
| Limit viscosity number: | $\eta = 733$ ml/g |
| Titratable nitrogen: | 3.06 mmol/g |
| Chloride determination: | 1.56% (= 0.44 mmol/g) |
| Degree of substitution: | |
| cationic groups | 0.14 |
| glycidol groups | 1.3 |

EXAMPLE 7

50 g (0.31 mol) of a high molecular chitosan with the characteristics data $\eta=1\,600$ ml/g and 76% free amine were dissolved in 5 liter water with the equimolar amount of hydrochloric acid and was subsequently precipitated with a sodium hydroxide solution by adjusting a pH value of 10. The precipitated and suctioned off water containing chitosan was stirred in a double casing stirring vessel of 2 liter content with 73.3 ml (1.1 mol) glycidol as well as 80.6 g glycidyl trimethyl ammonium chloride for 8 hours at 80° C. Thereafter, the further procedure was like described in example 6. The yield of the chitosan derivative was 85 g.

| Characteristics of the quaternary chitosan derivative | |
|---|---|
| Limit viscosity number: | $\eta = 710$ ml/g |
| Titratable nitrogen: | 3.2 mmol/g |
| Chloride determination: | 1.80 mmol/8 |
| Degree of substitution: | |
| cationic groups | 0.60 |
| glycidol groups | 2.1 |
| Steam absorption: | 12.2% |
| Pendulum hardness in accordance with Konig | 193 sec. |

EXAMPLE 8

Quaternisation of chitosan with 1-chlor-3-trimethylammonium-propanol-2-chloride 10 g (0.062 mol) chitosan ($\eta=140$ ml/g; free amine 86%) were stirred with 58 g (0.18 mol) 60% 1-chloro-3-trimethyl ammonium-propanol-2-chloride and 10 g (0.25 mol) sodium hydroxide in 100 ml water for 72 hours at 50° C. Susequently, the insoluble reaction product was suctioned off, washed with water and then stirred for 48 hours at 50° C. with 15 ml glycidol. The remaining water insoluble residue, consisting of nonreacted chitosan, was separted by centrifugation. The watery solution was decanted and dialyzed for 1 week. Subsequently, the solution was further processed as described in example 2. The yield on the quaternary chitosan derivate was 10.8 g.

| Characteristics of the quaternary chitosan derivative | |
|---|---|
| Limit viscosity number: | $\eta = 57$ ml/g |
| Titratable nitrogen: | 3.15 mmol/g |
| Chloride determination: | 0.5% (= 0.15 mmol/g) |
| Degree of substitution: | |
| cationic groups | 0.05 |
| glycidol groups | 1.9 |
| Steam absorption: | 21.1% |
| Pendulum hardness in accordance with Konig | 196 sec |

EXAMPLE 9

100 g (0.62 mol) chitosan with the same characteristics data as in example 2 was dispersed in 400 ml water. Glycidyl trimethyl ammonium chloride was added to this dispersion at a temperature of 80° C. by stirring in intervals of 2.5 hours 3 times 70 g each (0.5 mol). After a reaction time of 24 hours 250 ml (3.9 mol) glycidol were added to the reaction mixture and the mixture was again stirred for 24 hours at 80°. The clear solution of the reaction product was dialyzed for 1 week and then further processed as described in example 2. The yield on the quaternay chitosan derivative was 66.7 g.

| Characteristics data of the quaternary chitosan derivative | |
|---|---|
| Limit viscosity number: | $\eta = 43$ mol/g |
| Titratable nitrogen: | 2.64 mmol/g |
| Chloride determination: | 2.05 mmol/g |
| Degree of substitution: | |
| cationic groups | 0.8 |
| glycidol groups | 1.2 |

In the following, examples for cosmetic agents are given based on the novel quaternary chitosan derivatives:

EXAMPLE 10

| Hair strenghtener | |
|---|---|
| 0.6 g | quaternary chitosan derivative in accordance with example 2 ($\eta = 65$ ml/g, degree of substitution = cationic groups 0.22; glycidol groups 1.7) |
| 73.8 g | water |
| 25.0 g | isopropanol |
| 0.4 g | 10% formic acid |
| 0.2 g | perfume oil |
| 100.0 g | |

20 ml of this solution were distributed on washed, towel dried hair, the hair was set in customary manner and dried. With a good strengthening effect the hair showed, in comparison to a hair strengthner on the basis of chitosan/formic acid, a more pleasant and softer feel.

EXAMPLE 11

| Tinting strenghtener | |
|---|---|
| 1.00 g | quaternary chitosan derivative in accordance with example 7 ($\eta = 710$ ml/g, degree of substitution = cationic groups 0.60; glycidol groups 2.1) |
| 1.00 g | Lactic acid |
| 0.10 g | cetyl trimethyl ammonium chloride, 50% watery solution |
| 0.05 g | acid brown 4 (C.I. 41 805) |
| 97.85 g | water |

-continued

| Tinting strenghtener |
| --- |
| 100.00 g |

20 ml of this solution were distributed on the washed, towel dried hair and the hair was set and dried in the customary manner. Thereafter, the hair showed a light red-brown coloration.

EXAMPLE 12

| Tinting strenghtener | |
| --- | --- |
| 0.60 g | quaternary chitosan derivative in accordance with example 2 ($\eta$ = 65 ml/g, degree of substitution = kationic groups 0,22; glycidol groups 1,7) |
| 0.15 g | 1.4 Di($\beta$-hydroxyethylamino)-2-nitro-5-chlorobenzene |
| 25.00 g | ethanol |
| 74.25 g | water |
| 100.00 g | |

20 ml of this solution was applied on the washed, towel dry hair, the hair was then set and dried. The hairs were colored red-violet and strenthed.

EXAMPLE 13

| Anionic hair washing agent | |
| --- | --- |
| 1.00 g | quaternary chitosan derivatives in accordance with claim4 ($\eta$ = 51 ml/g, degree of substitution = cationic groups 0.6; glycidol groups 1.0) |
| 40.00 g | lauryl alcohol digykol ether sulfate-sodium-salt, 28% watery solution |
| 4.00 g | sodium chloride |
| 0.05 g | dye |
| 54.85 g | water |
| 0.10 g | formaldehyde, 25% watery solution |
| 100.00 g | |

A clear shampoo was obtained. The washed hair was excellently conditioned with respect to feel, shine and combability. Because of the compatibility of the quaternary chitosan derivatives with alkyl ether sulfate, the aforementioned shampoo can be made so that a simultaneous cleaning and caring for the hair is possible.

EXAMPLE 14

| Amphoteric, tinting hair washing agent | |
| --- | --- |
| 2.00 g | quaternary chitosan derivatives in accordance with example 4 ($\eta$ = 51 ml/g, degree of substitution = cationic groups 0.6; glycidol groups 1.0) |
| 40.00 g | dimethyl-carboxy methylene-propylene amido stearat betain, 35% watery solution |
| 5.06 g | formic acid, 10% |
| 3.50 g | coconut oil fatty acid diethanol amide |
| 1.00 g | picramic acid (C.I. 76 540), 1% aqueous soltuion |
| 48.44 g | water, fully desalted |
| 100.00 g | |

The hair was shampooed with about 15 to 20 g of the aforementioned agent. After a setting time of 5 to 10 minutes a rinsing with water was performed. The hair was tinted yellow-orange and excellently conditioned, in particular with respect to feel and combability.

EXAMPLE 15

| Hair treating agent | |
| --- | --- |
| 0.30 g | quaternary chitosan derivative in accordance with claim 7 ($\eta$ = 710 ml/g, degree of substitution = cationic groups 0.60; glycidol groups 2.1) |
| 4.00 g | cetyl stearyl alcohol |
| 1.48 g | lactic acid, 10% |
| 2.50 g | coco (pentaethoxy)methyl ammonium chloride |
| 1.00 g | sorbitol anmonopalmitate with 20 Mol ethylene oxide |
| 90.72 g | water, completely desalted |
| 100.00 | |

EXAMPLE 16

| Hair treating agent, gel-like | |
| --- | --- |
| 2.1 g | quaternary chitosan derivative in accordance with example 4 ($\eta$ = 51 ml/g, degree of substitutions = cationic groups 0.6; glycidol groups 1.0) |
| 0.6 g | hydroxy propyl methyl cellulose |
| 0.5 g | lauryl pyridinium chloride |
| 96.8 g | water, completely desalted |
| 100.0 g | (adjusted to pH 5.0 with 10% formic acid) |

35 g of the hair treating agent in accordance with example 15 or 16 were distributed in the washed hair and after a setting time of 3 to 5 minutes it was again rinsed out with water; as a result an excellent feel, shine as well as combability of the hair is obtained.

EXAMPLE 17

| Skin cream | |
| --- | --- |
| 0.30 g | quaternary chitosan derivative in accordance with example 2 ($\eta$ = 65 ml/g, degree of substitution = cationic groups 0.22; glycidol groups 1.7) |
| 3.00 g | stearyl alcohol |
| 1.00 g | wool fatty alcohol (adeps lanae) |
| 1.00 g | petrolatum |
| 0.76 g | lactic acid, 10% |
| 1.00 g | sodium cetyl stearyl sulfate |
| 92.94 g | water, completely desalted |
| 100.00 g | |

EXAMPLE 18

| Hair tinting agent | |
| --- | --- |
| 0.50 g | quaternary chitosan derivative in accordance with example 7 ($\eta$ = 710 ml/g, degree of substitution = cationic groups 0.60; glycidol groups 2.1) |
| 12.00 g | cetyl stearyl alcohol |
| 0.10 g | parahydroxy benzoic acid ethylester |
| 6.00 g | lauryl alcohol-digylcoleethersulfate sodium salt (28% watery solution) |
| 0.50 g | perfume oil |
| 79.31 g | water |
| 0.50 g | 1-hydroxy-2-amino-4-nitrobenzol (C.I.76 530) |
| 0.85 g | 1,4-diamino-2-nitrobenzol (C.I. 76 070) |
| 0.24 g | sodium hydroxide |
| 100.00 g | |

About 30 to 40 g were distributed in the washed hair and was rinsed out after a setting time of 20 minutes. The hair was colored reddish and had a good combability and a pleasant feel.

EXAMPLE 19

| Oxidation hair dyeing agent | |
|---|---|
| 0.50 g | quaternary chitosan derivative in accordance with example 7 (n = 710 ml/g, degree of substitution = cationic groups 0.60;0.60; glycidol groups 2.1) |
| 0.08 g | 3,5-diamino-2 6-dimethoxy pyridin-dihydrochloride |
| 0.30 g | 1,4-diamino benzene |
| 0.25 g | resorcin |
| 0.30 g | sodium salt |
| 3.50 g | lauryl alcohol-diglycole ether sulfate sodium salt (28% watery solution) |
| 15.00 g | cetyl alcohol |
| 3.00 g | ammonia |
| 77.07 g | water |
| 100.00 | |

50 g of this hair dyeing agent was admixed with 50 ml 6% hydrogen peroxide solution and was applied to white hair.

After 30 minutes the hair was rinsed with water and dried. The hair had a naturally looking mat-blond coloration as well as a natural pleasant feel.

EXAMPLE 20

| Permanent wave agent | |
|---|---|
| 0.5 g | quaternary chitosan derivative in accordance with example 7 ($\eta$ = 710 ml/g, degree of substitution = cationic groups 0.60; glycidol groups 2.1) |
| 1.00 g | thioglykolic acid |
| 8.0 g | ammonia, 25% |
| 6.1 g | ammonium hydrogen carbonate |
| 75.4 g | water |
| 100.0 g | |

This permanent wave agent was applied to the curlered towel dried hair in an even manner and it did set for 20 minutes; thereafter the hair was rinsed with water and treated oxidatively in known manner. A good wave result was obtained, while the hair felt natural and soft.

EXAMPLE 21

| Hair strengthener, alcohol free | |
|---|---|
| 0.7 g | quaternary chitosan derivative in accordance with example 8 ($\eta$ = 57 ml/g, degree of substitution = cationic groups 0.05; glycidol groups 1.9) |
| 1.5 g | formic acid 10% |
| 0.8 g | perfume |
| 0.1 g | chloracetamide perservative |
| 96.9 g | water, completely desalted |
| 100.0 g | |

20 ml of this solution were applied on the washed towel dried hair, the hair was then set and dried. The hair showed a pleasant soft touch, while having a good strengthening effect.

I claim:

1. A cosmetic composition for the treatment of hair or skin, characterized in that the active ingredient is a quaternary macromolecular polymer compound derived from chitosan having the formula $$HO[C_6H_{11-m}NO_4(R^1)_m(R^2)_n(R^3)_q]_pH,$$

wherein m denotes any given numerical value from 0 to 0.5, n denotes any given numerical value from 0 to 6, q is a given numerical value from 0.005 to 3.0, p denotes a whole number from 10 to 50,000, R' is an acetyl residue, $R^2$ represents a bivalent residue of the formula $-CH_2CH(OH)-CH_2-O-$,

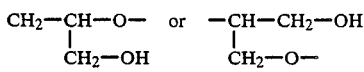

and $R^3$ is a bivalent residue of the formula

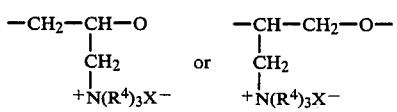

wherein $R^4 = C_1$ to $C_4$ alkyl and $X = Cl$, Br, I or $CH_3SO_4$, in a cosmetic carrier selected from the group consisting of water, an alcohol, an aqueous-alcoholic solution, a cream, a gel and an emulsion.

2. Composition in accordance with claim 1, characterized in that n in formula I denotes a numerical value of 1.0 to 2.1.

3. Composition in accordance with claim 1, characterized in that q in the formula I denotes a numerical value of 0.05 to 0.6.

4. Composition in accordance with claim 1, characterized in that it contains the polymer compound of formula I in an amount of from 0.05 to 10.0% by weight.

5. Composition in accordance with claim 1, further comprising cationic, nonionic, amphoteric or anionic tenside surfactant and provided in form of a shampoo.

6. Composition in accordance with claim 5, characterized in that the anionic tenside is an alkyl ether sulfate.

7. Composition in accordance with claim 6, characterized in that the tenside is contained therein in a concentration between 3 and 25% by weight and has a pH value between 4 and 7.

8. Composition in accordance with claim 1, characterized in that it contains as a cosmetic base an alcoholic or aqueous-alcoholic solution which is admixed with a pressurized propellant gas, is filled into a pressure container and is present as an aerosol hair spray.

9. Composition in accordance with claim 1, characterized in that the cosmetic base is water, alcoholic or aqueous-alcoholic solution, a cream, a gel or an emulsion, wherein the chitosan derivative of the formula I is contained in a concentration between 0.1 and 10% by weight, composition being for skin treatment.

10. Composition in accordance with claim 1, characterized in that it contains an additional film forming cosmetic polymer which is selected from the group consisting of shellac, alginates, gelatines, pectines, cellulose derivatives, polyvinylpyrrolidone, polyvinyl acetate, polymerisates of acrylic acid, polymerisates of methacrylic acid, basic polymerisates of esters of acrylic acid with amino alcohols, basic polymerizates of methacrylic acid with amino alcohols, salts of basic polymerisates of acrylic acid, salts of basic polymerisates of methacrylic acid, quaternisation products of basic polymerisates of acrylic acid, quaternisation products of basis polymerisates of methacrylic acid, polyacrylonitrile, and polyvinylpyrrolidone-vinylacetate.

11. Composition in accordance with claim 1, characterized in that the cosmetic base is water, alcoholic or aqueous-alcoholic solution or an emulsion further comprising additional hair dye and is present in the form of a dyeing strengthener or tinting strengthener.

12. Quaternary macromolecular polymer compound derived from chitosan of the general formula I $$HO[C_6H_{11-m}NO_4(R^1)_m(R^2)_n(R^3)_q]_pH,$$

wherein m denotes any given numerical value from 0 to 0.5, n denotes any given numerical value from 0 to 6, q is a given numerical value from 0.005 to 3.0, p denotes a whole number from 10 to 50,000, $R^1$ is an acetyl residue, $R^2$ represents a bivalent residue $-CH_2CH(OH)-CH_2-O-$, $$\begin{array}{c}CH_2-CH-O-\\|\\CH_2-OH\end{array} \text{ or } \begin{array}{c}-CH-CH_2-OH\\|\\CH_2-O-\end{array}$$

and $R^3$ is a bivalent residue $$\begin{array}{c}-CH_2-CH-O-\\|\\CH_2\\|\\{}^+N(R^4)_3X^-\end{array} \text{ or } \begin{array}{c}-CH-CH_2-O-\\|\\CH_2\\|\\{}^+N(R^4)_3X^-\end{array}$$

with $R^4 = C_1$- to $C_4$-alkyl and $X = Cl, Br, I$ or $CH_3SO_4$.

13. Compound in accordance with claim 12, characterized in that in formula I, n denotes a numerical value of 1.0 to 2.1, q represents a numerical value of 0.05 to 1.1 and the limit viscosity n has a value of 27 to 733 ml/g.

14. Compound in accordance with claim 12, characterized in that in formula I $n=0$ and $q=1.4$.

15. Compound in accordance with claim 12, characterized in that in formula I $R^4=CH_3$ and $X=Cl$.

* * * * *

UNITED STATES PATENT AND TRADEMARK OFFICE
CERTIFICATE OF CORRECTION

PATENT NO. : 4,822,598

DATED : April 18, 1989

INVENTOR(S) : G. Lang, H. Wendel, E. Konrad

It is certified that error appears in the above-identified patent and that said Letters Patent is hereby corrected as shown below:

Column 8, line 42, cancel "3.15 nmol/g" and substitute -- 3.15 mmol/g --;

column 8, line 53; cancel "[nmol/g]" and substitute --[mmol/g]--;

column 8, lines 57 and 58, cancel " $\bar{M} \frac{g}{[mol]} = \frac{1000}{Nt \frac{[nmol]}{g}}$ , and substitute -- $\bar{M} \frac{g}{[mol]} = \frac{1000}{Nt \frac{[mmol]}{g}}$ --;

column 11, line 42, cancel " 1.80 mmol/8" and substitute -- 1.80 mmol/g --;

column 13, line 32, cancel "claim 4" and substitute --example 4--;

column 14, line 11, cancel "sorbitol anmonopalmitate" and substitute --sorbitol monopalmitate--;

column 15, line 7, cancel "cationic groups 0.60;0.60; glycidol groups 2.1" and substitute --cationic groups 0.60; glycidol groups 2.1--;

column 15, line 8, cancel "3,5-diamino-2 6-dimethoxy pyridin-dihydrochloride" and substitute --3,5-diamino-2,6-dimethoxy pyridin-dihydrochloride;

column 15, line 10, cancel "sodium salt" and substitute --sodium sulfite--;

column 15, line 30, cancel "1.00 g thioglykolic acid" and substitute --10.0 thioglykolic acid--;

UNITED STATES PATENT AND TRADEMARK OFFICE
CERTIFICATE OF CORRECTION

PATENT NO. : 4,822,598

DATED : April 18, 1989

INVENTOR(S) : G. Lang, H. Wendel, E. Konrad

It is certified that error appears in the above-identified patent and that said Letters Patent is hereby corrected as shown below:

column 15, line 68, cancel "50,000, R' " and substitute --50,000,$R^1$--.

Signed and Sealed this

Twentieth Day of February, 1990

*Attest:*

JEFFREY M. SAMUELS

*Attesting Officer*   *Acting Commissioner of Patents and Trademarks*